(12) United States Patent
Katz

(10) Patent No.: US 6,623,723 B2
(45) Date of Patent: *Sep. 23, 2003

(54) METHOD FOR TREATING BRONCHIAL CONSTRICTION AND BRONCHOSPASM

(75) Inventor: Stanley E. Katz, Milltown, NJ (US)

(73) Assignee: Cellular Sciences Inc., Flemington, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/933,981

(22) Filed: Aug. 21, 2001

(65) Prior Publication Data

US 2003/0039615 A1 Feb. 27, 2003

(51) Int. Cl.[7] .............................. A61K 9/12; A61K 9/14; A61K 31/19
(52) U.S. Cl. .............................. 424/46; 424/45; 514/54; 514/557; 514/625; 514/826; 128/200.14; 128/203.15
(58) Field of Search ............... 424/46, 45; 514/557, 514/625, 826, 54; 128/200.14, 203.15

(56) References Cited

U.S. PATENT DOCUMENTS

| 5,714,515 A | * | 2/1998 | Bunger | 514/557 |
| 5,798,388 A | * | 8/1998 | Katz | 514/557 |
| 5,939,459 A | * | 8/1999 | Katz | 514/625 |
| 5,952,384 A | * | 9/1999 | Katz | 514/625 |
| 6,051,609 A | * | 4/2000 | Yu et al. | 514/557 |

* cited by examiner

Primary Examiner—Michael G. Hartley
Assistant Examiner—M. Haghighatian
(74) Attorney, Agent, or Firm—Richard R. Muccino

(57) ABSTRACT

The present invention is directed to a method for treating bronchial constriction in mammals. The method comprises contacting mammalian lung with a compound selected from the group consisting of pyruvate and pyruvate precursors. The compound is present in a therapeutically effective amount to produce bronchial dilation. The present invention is also directed to a method for treating airway disease in mammals. The method comprises contacting mammalian lung with a compound selected from the group consisting of pyruvate and pyruvate precursors. The compound is present in an amount from about 0.0001 millimoles to about 0.005 millimoles. The present invention is further directed to a method for treating airway disease in mammals. The method comprises contacting the mammalian lung with a compound selected from the group consisting of pyruvate and pyruvate precursors. The compound is present in a therapeutically effective amount to prevent bronchial spasm. The present invention is still further directed to a method for treating airway disease in mammals. The method comprises contacting the mammalian lung with a compound selected from the group consisting of pyruvate and pyruvate precursors. The compound is present in a therapeutically effective amount to prevent bronchial constriction.

25 Claims, 3 Drawing Sheets

METHOD FOR TREATING BRONCHIAL CONSTRICTION AND BRONCHOSPASM

FIELD OF THE INVENTION

This invention pertains to therapeutic methods of preventing and treating bronchial spasm and bronchial constriction. This invention also pertains to compounds used in the therapeutic methods.

BACKGROUND OF THE INVENTION

More than 17 million people in the U.S. now have asthma, an increase of more than 75 percent since 1980. As the number of patients has risen, so have the larger consequences of the disease. Today, asthma is one of the top reasons for hospitalization of children. It causes children to miss more than 10 million school days a year and adults to miss 3 million days at work. It is responsible for more than 10 million doctor visits a year. It is estimated that asthma will be responsible for more than 5,600 deaths this year, more than twice as many as 20 years ago.

Chronic Obstructive Pulmonary Disease (COPD) is a blockage of airflow out of the lungs. COPD encompasses emphysema, alpha antritrypsin deficiency-related (AAT) emphysema, and chronic bronchitis. Nearly 16 million Americans suffer from COPD, which is the fourth leading cause of death, claiming the lives of nearly 87,000 Americans annually.

Smoking causes approximately 80 to 90 percent of COPD cases; a smoker is 10 times more likely than a nonsmoker to die of COPD. Other known causes are frequent lung infections and exposure to air pollutants. Depending on the severity of the disease, treatments may include bronchial dilators which open up air passages in the lungs; antibiotics; and exercise to strengthen muscles. People with COPD may eventually require supplemental oxygen and may have to rely on mechanical respiratory assistance.

Emphysema causes irreversible lung damage. The walls between the air sacs within the lungs lose their ability to stretch and recoil. They become weakened and break. Elasticity of the lung tissue is lost, causing air to be trapped in the air sacs and impairing the exchange of oxygen and carbon dioxide. An estimated 1.9 million Americans have emphysema.

Symptoms of emphysema include cough, shortness of breath and an increased effort to breathe. Diagnosis is by pulmonary function tests, along with the patient's history, examination and other tests. The quality of life for a person suffering from emphysema diminishes as the disease progresses. At the onset, there is minimal shortness of breath. Eventually, there is severe shortness of breath often leading to the total dependency on the administration of oxygen around the clock.

Alpha antitrypsin deficiency-related (AAT) emphysema, also called "early onset emphysema," is caused by the inherited deficiency of a protein called alpha 1-antitrypsin (AAT) or alpha-protease inhibitor. AAT, produce by the liver, is a "lung protector." In the absence of AAT, emphysema is inevitable. An estimated 50,000 to 100,000 American have AAT deficiency emphysema, primarily of northern European descent.

The onset of AAT deficiency emphysema is characterized by shortness of breath, decreased exercise capacity. Blood screening is used if the trait is known to be in the family and will determine if a person is a carrier or AAT-deficient. If children are diagnoses as AAT-deficient through blood screening, they may undergo a liver transplant to prevent the onset of AAT deficiency emphysema in their adult life.

Chronic bronchitis is an inflammation of the lining of the bronchial tubes. An estimated 13.8 million people suffer from chronic bronchitis, the sixth leading chronic condition in America. Whereas emphysema is more concentrated in the elderly, chronic bronchitis affects people of all ages. Symptoms include chronic cough, increased mucus, frequent clearing of the throat and shortness of breath. It may precede or accompany pulmonary emphysema. Treatments aimed at reducing irritation in the bronchial tubes include antibiotics and bronchial dilators.

Airway diseases such as asthma, acute bronchitis, emphysema, chronic obstructive emphysema, centrilobular emphysema, panacinar emphysema, chronic obstructive bronchitis, reactive airway disease, cystic fibrosis, bronchiectasis, acquired bronchiectasis, kartaagener's syndrome, atelectasis, acute atelectasis, chronic atelectasis, pneumonia, legionnaires disease, psittacosis, fibrogenic dust disease, diseases due to organic dust, diseases due to irritant gases and chemicals, hypersensitivity diseases of the lung, idiopathic infiltrative diseases of the lungs and the like are generally characterized by cough, shortness of breath and an increased effort to breath.

U.S. Pat. Nos. 5,798,388; 5,939,459 and 5,952,384 issued to Katz. The Katz inventions pertain to a method for treating various disease states in mammals caused by mammalian cells involved in the inflammatory response and compositions useful in the method. The method comprises: contacting the mammalian cells participating in the inflammatory response with an inflammatory mediator; wherein the inflammatory mediator is present in an amount capable of reducing the undesired inflammatory response and is an antioxidant. The preferred inflammatory mediator is a pyruvate. Katz discloses the treatment of airway diseases of the lungs such as bronchial asthma, acute bronchitis, emphysema, chronic obstructive emphysema, centrilobular emphysema, panacinar emphysema, chronic obstructive bronchitis, reactive airway disease, cystic fibrosis, bronchiectasis, acquired bronchiectasis, kartaagener's syndrome, atelectasis, acute atelectasis, chronic atelectasis, pneumonia, essential thrombocytopenia, legionnaires disease, psittacosis, fibrogenic dust disease, diseases due to organic dust, diseases due to irritant gases and chemicals, hypersensitivity diseases of the lung, idiopathic infiltrative diseases of the lungs and the like by inhaling pyruvate containing compositions. The pyruvate acts as an inflammatory response mediator and reduces the undesired inflammatory response in mammalian cells.

U.S. Pat. No. 5,296,370 (Martin et al.) discloses therapeutic compositions for preventing and reducing injury to mammalian cells and increasing the resuscitation rate of injured mammalian cells. In one embodiment, the therapeutic composition comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the resuscitation of injured mammalian cells.

While the above therapeutic compositions and methods are reported to treat various conditions, none of the compositions and methods disclose or teach the bronchial dilating or bronchial spasm preventing properties of low doses of pyruvate or pyruvate precursors nor do they disclose methods of treating airway diseases with a bronchial dilating effective amount or bronchial spasm preventing amount of a pyruvate or pyruvate precursor.

SUMMARY OF THE INVENTION

The present invention pertains to a method for treating an airway condition in mammals which may be characterized by one or more of the following most common symptoms: chronic cough, increased mucus, frequent clearing of the throat, wheezing, chest tightness, coughing, gasping for breath, shortness of breath and other conditions related to bronchial constriction and bronchial spasm. The method for treating such airway condition in mammals comprises contacting the lungs with a compound selected from the group consisting of pyruvate and a pyruvate precursor; wherein the compound is present in an amount capable of producing bronchial dilation. The invention further comprises a method for treating airway condition in mammals which comprises contacting the mammalian lung with a compound selected from the group consisting of pyruvate and pyruvate precursor; wherein the compound is present in a therapeutically effective amount to prevent bronchial spasm.

DETAILED DESCRIPTION OF THE INVENTION

Figure 1:
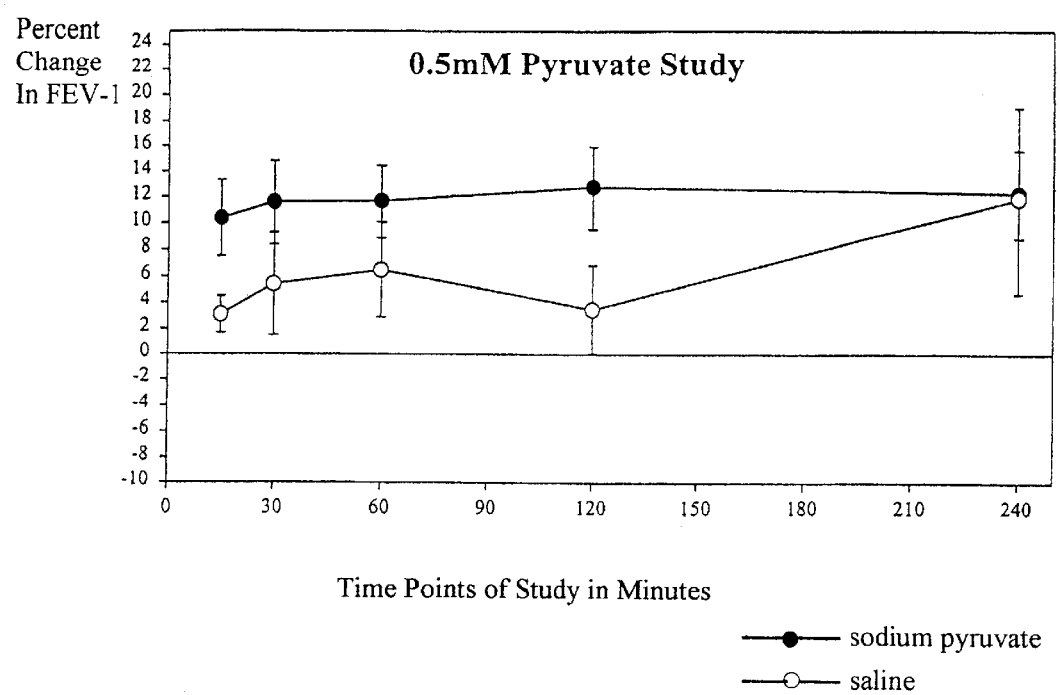
FIG. 1 is a graphical illustration of percent change in FEV-1 measurements post administration of placebo or sodium pyruvate 0.5 mM to asthmatic subjects.

Conditions having the symptoms of chronic cough, increased mucus, frequent clearing of the throat, wheezing, chest tightness, coughing, gasping for breath, shortness of breath and other conditions related to bronchial constriction and bronchial spasm are often caused by over reaction to a stimuli. Such a stimuli can be classed as a trigger or an inducer and vary from person to person. The triggers irritate the airways and result in bronchial constriction and bronchial spasm. Common triggers include but are not limited to: cold air, dust, strong fumes, exercise, inhaled irritants, emotional upsets and smoke. Inducers may also cause bronchial constriction. Typical inducers include allergens and respiratory viral infections. Allergens include but are not limited to: pollen, animal secretions, molds and house dust mites. Exposure to inducers not only results in bronchial constriction, but can also lead to inflammation and serious lung disorders.

During bronchial constriction, the muscles in the bronchial tubes constrict, causing difficulty in breathing. Airflow through these passages becomes difficult resulting in labored breathing. This is often followed by increased mucous secretions, which further plug the airways. Bronchial constriction and increased mucus may result in cough and wheezing. With less and less air available through the lungs, oxygen in the blood decreases.

It has been found that low doses of pyruvate act as a bronchial dilator in mammals with bronchial constriction; whereas high doses of pyruvate do not act as a bronchial dilator. It is believed that when low concentration levels of pyruvate are applied to lung tissue, pyruvate acts outside of the lung cells. Without being held to a specific theory of operation, it is believed that the extra cellular pyruvate acts as a reactive oxygen species antagonist reducing the active oxygen species present in the lung. It is believed these reactive oxygen species are either directly or indirectly responsible for bronchial constriction and bronchial spasm. When the active oxygen agents are removed, the lungs return to normal. In reducing the active oxygen species present in the lung, pyruvate is consumed. When low levels of pyruvate were employed to treat lungs, there would be little or no residual pyruvate available to enter lung cells. When high levels of pyruvate are employed to treat lungs, the reactive oxygen species are inactivated but the presence of excess pyruvate in the airway results in maintaining bronchial constriction. Bronchial spasm is a series of short duration bronchial constrictions alternating with periods of bronchial relaxation.

In a preferred embodiment, the therapeutic compositions containing the bronchial dilator are administered locally to the bronchi. In another preferred embodiment, the therapeutic compositions are administered systemically. In yet another preferred embodiment, the therapeutic compositions are administered systemically and locally concomitantly.

In a preferred embodiment, the therapeutic compositions are administered by inhalation. The therapeutic compositions may be first nebulized by any suitable means. The means of delivering the medicine to the lungs may be for example by nebulizer or metered dose inhalers (MDI's). Such MDI's may use propellants such as gases or they may be dry powder inhalers or mini-nebulizers. The therapeutic compositions may be in liquid or solid form with liquid droplets or particle size being small enough to facilitate access to the bronchi by inhalation.

In another preferred embodiment, a sterile solution of bronchial dilator is nebulized and inhaled by the patient. A therapeutically effective amount of bronchial dilator is inhaled. This may be accomplished in a single inhalation or by repeated inhalations over a period of time of about 1 to 30 minutes. Preferably, inhalation will be complete in less than 20 minutes. Most preferably inhalation will be complete in less than 15 minutes.

The preferred bronchial dilator is at least one compound selected from the group consisting of a pyruvate precursor and pyruvate. A precursor is a substance from which another substance is formed and in this text also includes salts. The preferred bronchial dilator will prevent bronchial spasm.

Preferably the pyruvate is selected from the group consisting of pyruvic acid, lithium pyruvate, sodium pyruvate, potassium pyruvate, magnesium pyruvate, calcium pyruvate, zinc pyruvate, manganese pyruvate, and the like and mixtures thereof. Sodium pyruvate is most preferred.

Another preferred bronchial dilator is selected from the group pyruvate precursors consisting of pyruvyl-glycine, pyruvyl-cystine, pyruvyl-alanine, pyruvyl-leucine, pyruvyl-valine, pyruvyl-isoleucine, pyruvyl-phenylalanine and pyruvamide.

Compositions for treating airway disease in mammals comprise: a bronchial dilator; and a carrier composition. The carrier composition is selected from the group consisting of tablets, capsules, powders, liquids, isotonic liquids, isotonic media, powders, microparticulates and the like.

The bronchial dilator is administered in a therapeutically effective amount to reduce the undesired bronchial constriction. In the typical case, the bronchial dilator is administered from about 0.0001 to about 0.005 millimoles per dose, preferably about 0.0005 to about 0.005 millimole per dose more preferably about 0.0005 to about 0.004 millimoles per dose, still more preferably about 0.0005 to about 0.0035 millimoles per dose and most preferably about 0.0005 to about 0.003. A millimole of pyruvate is the equivalent weight of one millimole of pyruvate anion or approximately 109 mg. A 5 ml solution of 0.5 millimolar concentration pyruvate will contain 0.0025 millimoles of pyruvate.

Bronchial spasm is treated by administering the bronchial dilator in a therapeutically effective amount to reduce the undesired bronchial constriction. In the typical case, the bronchial dilator is administered from about 0.0001 to about 0.005 millimoles per dose, preferably about 0.0005 to about 0.005 millimole per dose more preferably about 0.0005 to about 0.004 millimoles per dose, still more preferably about 0.0005 to about 0.0035 millimoles per dose and most preferably about 0.0005 to about 0.003. A millimole of pyruvate is the equivalent weight of one millimole of pyruvate anion or approximately 109 mg. A 5 ml solution of 0.5 millimolar concentration pyruvate will contain 0.0025 millimoles of pyruvate.

Typical airway diseases causing bronchial spasm, bronchial constriction or both treatable by the present compositions and method include but are not limited to acute bronchitis, asthma, emphysema, chronic obstructive emphysema, chronic obstructive pulmonary disease, centrilobular emphysema, panacinar emphysema, chronic obstructive bronchitis, reactive airway disease, cystic fibrosis, bronchiectasis, acquired bronchiectasis, interstitial lung disease, kartaagener's syndrome, atelectasis, acute atelectasis, chronic atelectasis, pneumonia, legionnaires disease, psittacosis, fibrogenic dust disease, diseases due to organic dust, diseases due to irritant gases and chemicals, hypersensitivity diseases of the lung, idiopathic infiltrative diseases of the lungs, chronic obstructive pulmonary disease and the like.

The bronchial dilator of the present invention may be administered prior to, after and/or with other therapeutic agents. Typical therapeutic agents are antibacterials, antivirals, antifungals, antihistamines, bronchial dilators, leukotriene receptor antagonists, proteins, enzymes, hormones, nonsteroidal anti-inflammatories, cytokines, steroids, and the like.

It is understood that the method of administration and the condition being treated will greatly affect the dose required to achieve the desired therapeutic effect. A mild asthmatic would be expected to respond to a lower dose than a severe asthmatic.

EXAMPLE

Response of Mild Asthmatics to Pyruvate Treatment

Three concentrations of sodium pyruvate were studied; 0.5 mM, 1.5 mM and 5.0 mM. Sixty (60) subjects completed the study protocol. The 60 subjects included fifteen (15) non-asthmatic control individuals and forty-five (45) individuals with mild bronchial asthma. Subjects with mild bronchial asthma all had a clinical diagnosis of the disease and at the Screening Visit (Visit 1) demonstrated either an FEV-1 between 60–80% of predicted or a greater than or equal to 12% increase in FEV-1 post inhalation of a bronchial dilator. The total subject population was composed of 40 females and 20 males with a mean population age of 36.6 years (range of 18–66 years).

The non-asthmatic control individuals were divided into three groups of five subjects. Each group received one of the three concentrations of sodium pyruvate.

Individuals with mild bronchial asthma were divided into three groups of 15 subjects; each group received one of the three concentrations of sodium pyruvate. Each subject each inhaled a single dose of physiological saline (Visit 1) and on a return visit inhaled a single dose of 5.0 ml of one of the concentrations of sodium pyruvate (Visit 2).

Expired breath was collected 1 hour prior to and 1 hour post inhalation of either physiological saline or sodium pyruvate.

Lung function assessments and vital signs were monitored at baseline (pre-dose) and at 15 minutes, 30 minutes 1 hour, 2 hours and 4 hours post administration. On a return visit (Visit 2), each subject inhaled a single 5 ml dose of sodium pyruvate in physiological saline. The physiological lung functions assessed included Forced Expiratory Volume in One Second (FEV-1) and Peak Expiratory Flow (PEF).

An FEV-1 and PEF values are obtained during routine spirometry testing. FEV-1 is the volume of air expelled in the first second of a forced expiration starting from full inspiration. It is the most widely accepted indicator of obstructive lung disease severity and used because it is objective and reproducible. PEF is the greatest flow rate that can be sustained for 10 milliseconds on forced expiration from full inflation of the lungs. Changes of greater than 10% FEV-1 and greater than 25% in PEF are generally accepted as clinically relevant ant were used as standards in data evaluation for this study.

Results:

FEV-1

A statistically significant improvement (greater than 10%) in percent change in FEV-1 was observed at 15 minutes (p=0.012), 30 minutes (p=0.039), 1 hour (p=0.054) and 2 hours (p=0.0001) after the inhalation of 0.5 mM sodium pyruvate as compared to the inhalation of physiological saline. FIG. 1.

PEF

Figure 2:
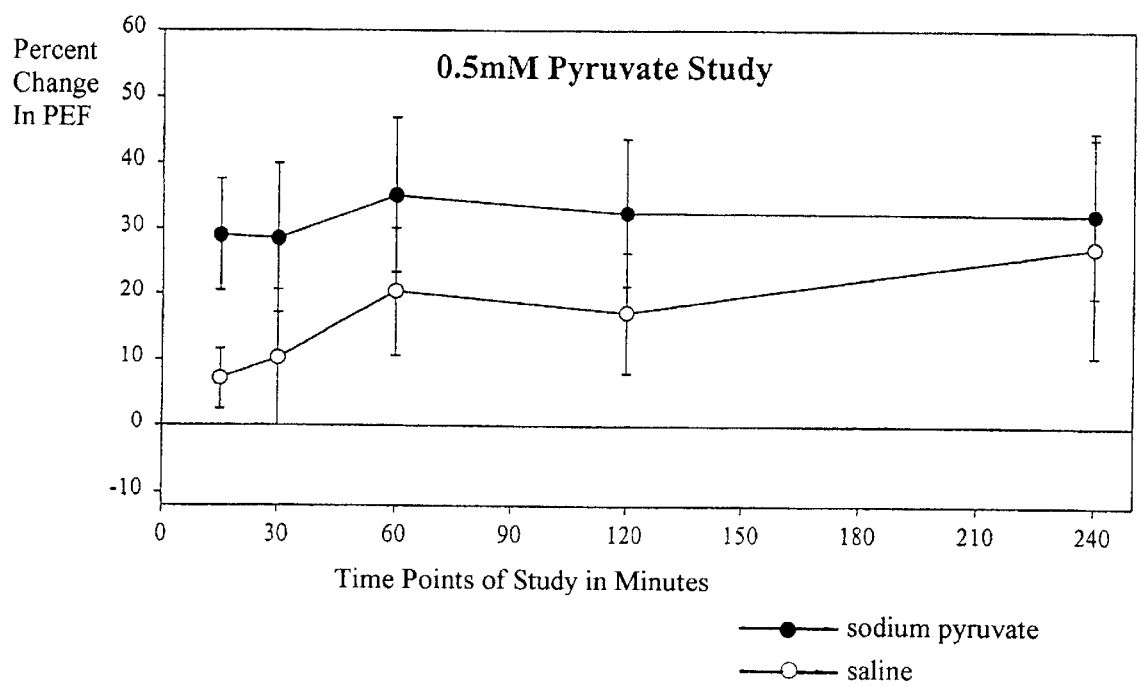
FIG. 2 is a graphical illustration of percent change in PEF measurements post administration of placebo or sodium pyruvate 0.5 mM to asthmatic subjects.

A statistically significant improvement (greater than 25%) in percent in PEF was observed at 15 minutes (p=0.014), 30 minutes (p=0.027), 1 hour (p=0.012), 2 hours (p=0.024), 4 hours (p=0.018) after the inhalation of 0.5 mM sodium pyruvate as compared to the inhalation of physiological saline. FIG. 2.

Figure 3:
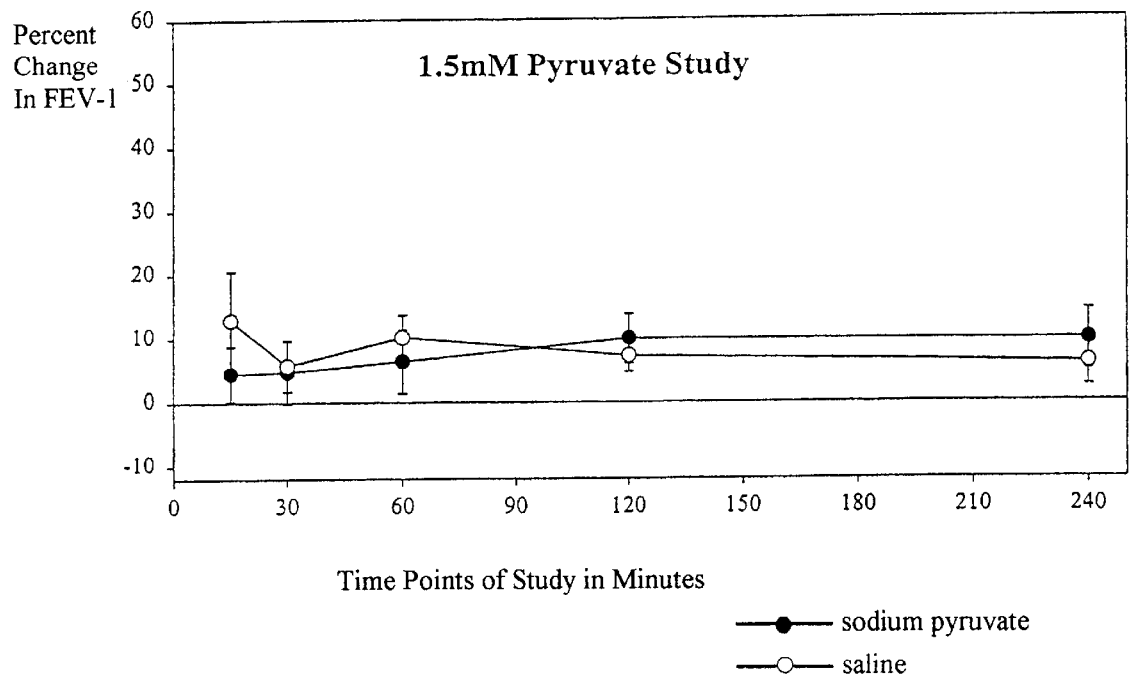
FIG. 3 is a graphical illustration of percent change in FEV-1 measurements post administration of placebo or sodium pyruvate 1.5 mM to asthmatic subjects.
Figure 4:
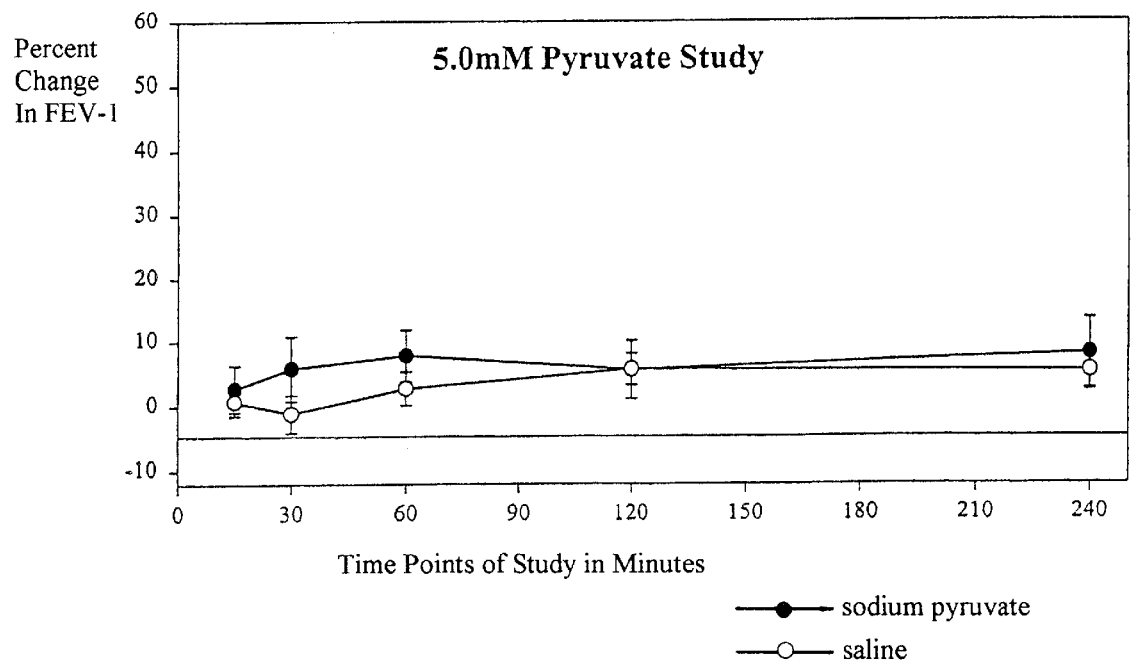
FIG. 4 is a graphical illustration of percent change in FEV-1 measurements post administration of placebo or sodium pyruvate 5.0 mM to asthmatic subjects.

No significant change in FEV-1 was observed in subjects with mild bronchial asthma after the inhalation of sodium pyruvate at either the 1.5 mM or 5.0 mM concentrations. FIGS. 3 and 4.

Figure 5:
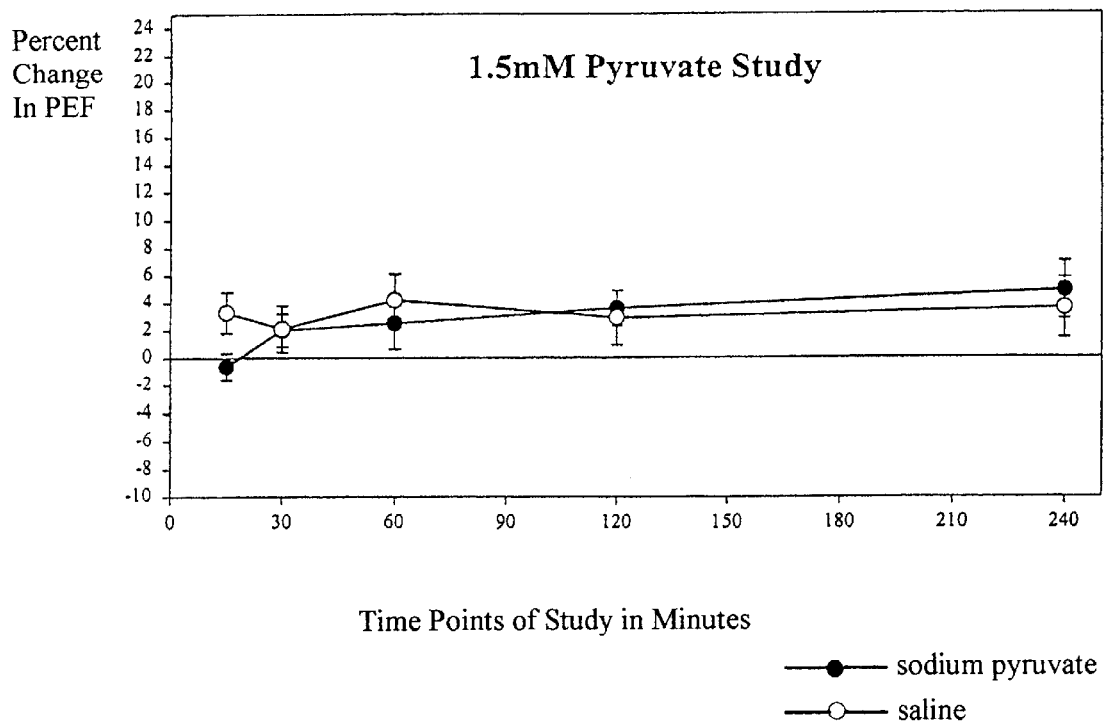
FIG. 5 is a graphical illustration of percent change in PEF measurements post administration of placebo or sodium pyruvate 1.5 mM to asthmatic subjects.
Figure 6:
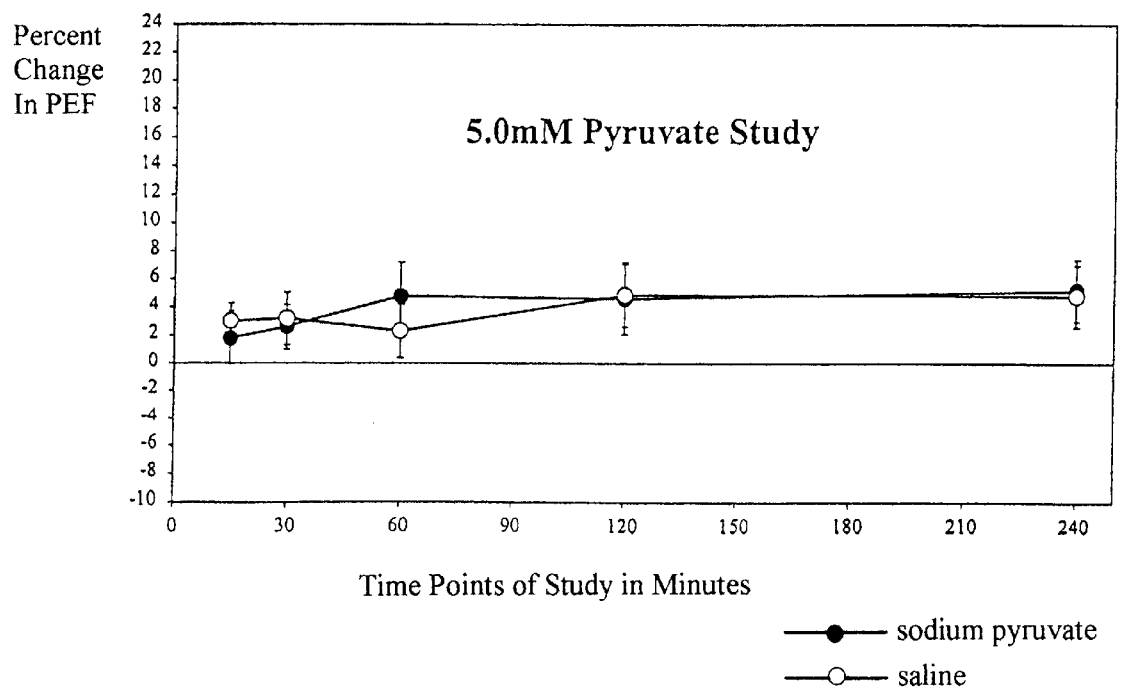
FIG. 6 is a graphical illustration of percent change in PEF measurements post administration of placebo or sodium pyruvate 5.0 mM to asthmatic subjects.

No significant change in PEF was observed in subjects with mild bronchial asthma after the inhalation of sodium pyruvate at either the 1.5 mM or 5.0 mM concentrations. FIGS. 5 and 6.

While the method for treating the bronchial constriction or bronchial spasm herein described constitute preferred embodiments of this invention, it is to be understood that the invention is not limited to this precise form of method and that changes may be made therein without departing from the scope of the invention which is defined in the appended claims.

I claim:

1. A method for treating bronchial constriction in mammals comprising contacting mammalian lung with a compound selected from the group consisting of pyruvate and pyruvate precursors; wherein the compound is present in a therapeutically effective amount to produce bronchial dilation.

2. The method of claim 1 wherein the compound is inhaled.

3. The method of claim 1 wherein the compound is present in an amount from about 0.0001 millimoles to about 0.005 millimoles.

4. The method of claim 1 wherein the compound is present in an amount from about 0.0005 millimoles to about 0.005 millimoles.

5. The method of claim 1 wherein the compound is present in an amount from about 0.0005 millimoles to about 0.004 millimoles.

6. The method of claim 1 wherein the compound is present in an amount from about 0.0005 millimoles to about 0.0035 millimoles.

7. The method of claim 1 wherein the compound is present in an amount from about 0.0005 millimoles to about 0.003 millimoles.

8. The method of claim 1 wherein the compound is present in an amount from about 0.001 millimoles to about 0.0035 millimoles.

9. The method of claim 1 wherein the pyruvate is selected from the group consisting of pyruvic acid, lithium pyruvate, sodium pyruvate, potassium pyruvate, magnesium pyruvate, calcium pyruvate, zinc pyruvate, manganese pyruvate, and mixtures thereof.

10. The method of claim 1 wherein the pyruvate precursor is selected from the group consisting of, pyruvyl-glycine, pyruvyl-alanine, pyruvyl cystine, pyruvyl-leucine, pyruvyl-valine, pyruvyl-isoleucine, pyruvyl-phenylalanine, pyruvamide, and salts of pyruvic acid.

11. The method of claim 1 further comprising contacting the mammalian lung with a therapeutic agent.

12. The method of claim 11 wherein the therapeutic agent is administered prior to the compound.

13. The method of claim 11 wherein the therapeutic agent is administered concomitantly with administration of the compound.

14. The method of claim 11 wherein the therapeutic agent is administered after administration of the compound.

15. The method of claim 11 wherein the therapeutic agent is one or more agents selected from the group consisting of antibacterial, antivirals, antifungals, antihistamines, bronchial dilators, leukotriene receptor antagonists, proteins, enzymes, hormones, nonsteroidal anti-inflammatories, cytokines and steroids.

16. A method for treating airway disease in mammals comprising contacting mammalian lung with a compound selected from the group consisting of pyruvate and pyruvate precursors; wherein the compound is present in an amount from about 0.0001 millimoles to about 0.005 millimoles.

17. A method for treating airway disease in mammals comprising contacting mammalian lung with a compound selected from the group consisting of pyruvate and pyruvate precursors; wherein the compound is present in a therapeutically effective amount to prevent bronchial spasm.

18. The method of claim 17 wherein the compound is inhaled.

19. The method of claim 17 wherein the compound is present in an amount from about 0.0001 millimoles to about 0.005 millimoles.

20. The method of claim 17 wherein the compound is present in an amount from about 0.0005 millimoles to about 0.005 millimoles.

21. The method of claim 17 wherein the compound is present in an amount from about 0.0005 millimoles to about 0.004 millimoles.

22. The method of claim 17 wherein the compound is present in an amount from about 0.0005 millimoles to about 0.0035 millimoles.

23. The method of claim 17 wherein the compound is present in an amount from about 0.0005 millimoles to about 0.003 millimoles.

24. The method of claim 17 wherein the compound is present in an amount from about 0.001 millimoles to about 0.0035 millimoles.

25. A method for treating airway disease in mammals comprising contacting mammalian lung with a compound selected from the group consisting of pyruvate and pyruvate precursors; wherein the compound is present in a therapeutically effective amount to prevent bronchial constriction.

* * * * *